(12) United States Patent
Matthes et al.

(10) Patent No.: US 10,555,800 B2
(45) Date of Patent: Feb. 11, 2020

(54) RECEIVER

(71) Applicant: Wittenstein SE, Igersheim (DE)

(72) Inventors: Michael Matthes, Igersheim (DE); Sebastian Hammel, Assamstadt (DE)

(73) Assignee: Wittenstein SE, Igersheim (DE)

( * ) Notice: Subject to any disclaimer, the term of this patent is extended or adjusted under 35 U.S.C. 154(b) by 259 days.

(21) Appl. No.: 15/451,536

(22) Filed: Mar. 7, 2017

(65) Prior Publication Data

US 2017/0252143 A1 Sep. 7, 2017

(30) Foreign Application Priority Data

Mar. 7, 2016 (DE) .................. 10 2016 104 115

(51) Int. Cl.
*A61F 2/02* (2006.01)
*H02J 50/10* (2016.01)
*H01F 38/14* (2006.01)

(52) U.S. Cl.
CPC ................ *A61F 2/02* (2013.01); *H01F 38/14* (2013.01); *H02J 50/10* (2016.02)

(58) Field of Classification Search
None
See application file for complete search history.

(56) References Cited

U.S. PATENT DOCUMENTS

| | | | |
|---|---|---|---|
| 8,521,303 B2 | 8/2013 | Solzbacher et al. | |
| 2002/0177884 A1 | 11/2002 | Ahn et al. | |
| 2004/0082977 A1 | 4/2004 | Engmark et al. | |
| 2011/0181420 A1* | 7/2011 | Mack | A42B 3/046 340/573.1 |
| 2011/0270349 A1 | 11/2011 | Cowley et al. | |
| 2011/0285348 A1* | 11/2011 | Hong | H01F 5/003 320/108 |
| 2013/0140370 A1* | 6/2013 | Finn | G06K 19/07769 235/492 |
| 2013/0199027 A1* | 8/2013 | Singh | H02J 17/00 29/602.1 |

(Continued)

FOREIGN PATENT DOCUMENTS

DE 10 2010 047 738 A1 3/2012
DE 10 2011 053 638 A1 3/2013

(Continued)

OTHER PUBLICATIONS

German search report for Application No. 10 2016 104 115.7 dated Nov. 28, 2016.

(Continued)

*Primary Examiner* — Jared Fureman
*Assistant Examiner* — Joel Barnett
(74) *Attorney, Agent, or Firm* — Bachman & LaPointe, PC

(57) ABSTRACT

Receiver (1), in particular an implantable receiver (1) for transmitting energy to an implant, with a multi-layer circuit board comprising a plurality of electrically conductive layers (11-16), wherein the circuit board comprises an outer coil area and a multi-layer inner area enclosed by the coil area, a coil which is integrally incorporated at least partially in the layers (11-16) of the circuit board in the coil area, wherein the number of the layers (11-16) of the circuit board is smaller within this inner area than in the coil area.

11 Claims, 2 Drawing Sheets

(56) References Cited

U.S. PATENT DOCUMENTS

| | | | | |
|---|---|---|---|---|
| 2015/0025613 A1* | 1/2015 | Nyberg, II | ............. | H01Q 1/273 |
| | | | | 607/137 |
| 2015/0170017 A1* | 6/2015 | Murayama | ........... | H01Q 1/2283 |
| | | | | 235/488 |
| 2015/0295416 A1* | 10/2015 | Li | ........................... | H01F 38/14 |
| | | | | 307/104 |

FOREIGN PATENT DOCUMENTS

| | | |
|---|---|---|
| DE | 20 2012 000 166 U1 | 6/2013 |
| WO | 02094370 A1 | 11/2002 |
| WO | 2009108233 A1 | 9/2009 |

OTHER PUBLICATIONS

European search report for patent application No. 17159192.8-1666 dated Jun. 30, 2017.

* cited by examiner

RECEIVER

FIELD OF THE INVENTION

The invention relates to a receiver, in particular an implantable receiver for transmitting energy to an implant, an implantable system, and a method for producing a receiver.

PRIOR ART

The prior art discloses implantable receivers for implants, comprising a coil for receiving energy or signals. In known receivers, a coil made of copper enamel wire is soldered onto the printed circuit board and adhesively bonded to the printed circuit board. On account of the size and number of the electrical parts, two printed circuit boards are typically needed which are placed on each other manually and have to be connected with pins. This entails a large number of assembly steps, and these steps are also susceptible to error.

U.S. Pat. No. 8,521,303 describes an example of an implantable coil arrangement from the prior art. The planar coil shown there is integrated in a polymer matrix and can comprise a large number of coil layers. However, the arrangement shown with coil is relatively large.

DISCLOSURE OF THE INVENTION

The object of the invention is to make available a receiver that is improved in relation to the prior art, and to make available an improved method for producing a receiver. The receiver should in particular be more compact or less expensive to produce.

The object is achieved, for example, by a receiver according to claim 1 or by a method according to the additional independent claim. Developments of the method or of the device are set forth in the dependent claims.

A first aspect concerns a receiver, in particular an implantable receiver for transmitting energy to an implant, with a multi-layer circuit board comprising a plurality of electrically conductive layers, wherein the circuit board comprises an outer coil area and a multi-layer inner area enclosed by the coil area, a coil which is integrally incorporated at least partially in the layers of the circuit board in the coil area, wherein the number of the layers of the circuit board is smaller within this inner area than in the coil area.

A further aspect concerns an implantable system with a receiver, in one of the typical embodiments described herein, and with an electromechanical implant.

A further aspect concerns a method for producing a receiver, in particular an implantable receiver for transmitting energy to an implant comprising a circuit board, by: producing a multi-layer base membrane of the circuit board with a plurality of layers, building up further layers on an upper side and/or an underside of the base membrane, wherein turns of a coil are integrated at least in some of the further layers in the coil area, and creating an upper cavity or a lower cavity from the further layers in the inner area to the inside of the coil area, by removing the further layers in the inner area, e.g. by milling or grinding.

Receivers in some embodiments are implantable, for example subcutaneously or close to or on a bone.

One or more insulating sheets are typically provided per conductive layer. For example, the circuit board structure can be formed by conductive layers alternating with insulating sheets. The lowermost layer or the uppermost layer can lie exposed or can be covered with a further insulating sheet.

By means of the larger number of the layers in the coil area, an upper cavity is typically formed, which is delimited by an upper rim. The upper rim is typically formed at least partially by the further layers in the coil area that are provided above a base membrane. The base membrane typically comprises the inner area and the outer area. In typical embodiments, only the base membrane of the circuit board is present in the inner area, whereas, in the coil area, further layers can be formed above or also additionally below the base membrane. The further layers on the underside in the coil area typically form a lower rim.

Coil turns are typically formed in the coil area. This permits a space-saving and protected arrangement of the turns in the layers in the coil area. In typical embodiments, between 3 and 15 turns are provided per layer, in particular between 5 and 10 turns per layer or, in particular, exactly 7 turns per layer. In typical embodiments, the coil area comprises three or more layers, for example at least two layers of the base membrane or at least two further layers in the coil area. At least 3 or at least 4 layers are typically present in the base membrane or in the inner area. At most 6 layers or at most 10 layers are typically provided in the base membrane or in the inner area. In typical embodiments, at least 8 further layers or at least 12 further layers are arranged in the coil area. In typical embodiments, at most 16 further layers or at most 25 further layers are present in the coil area.

Typical receivers are suitable for an electro-mechanical implant. Typical electromechanical implants are in particular distractors, which are suitable for example for the treatment of long tubular bones or of scoliosis. The receiver is typically designed to provide energy for an electric drive machine of an active implant, for example a rating of at least 0.1 Watt or at least 0.5 Watt. Typical embodiments are suitable for powering active implants, active typically being understood as meaning that the implant can typically perform a movement or typically comprise a drive motor.

In typical methods for producing a receiver, the further layers are applied both in the inner area and also in the coil area. A typical layer of the layers of the base membrane or also of the further applied layers comprises conductor tracks or typically one conductive sheet per layer.

In typical methods, by milling out the inner area, an upper rim is formed in the coil area and the upper cavity is formed in the inner area. Moreover, a lower rim can additionally be formed in the coil area, and the lower cavity can be formed on the underside in the inner area.

Typically, the inner area comprises at most half as many, or less than half as many, layers as the coil area. In this way, an upper cavity is created, and optionally also a lower cavity, for receiving electronic components.

In typical embodiments, the coil area, on the upper side of the circuit board, forms an upper rim around the inner area, wherein electronic components are arranged on the upper side of the circuit board in the inner area. Typically, a maximum height of the electronic components on the upper side is at most twice, typically at most 1.5 times or at most 1.2 times or at most 1.1 times as high as the step between coil area and inner area on the upper side. This step corresponds to the height between the upper side of the base membrane and the top edge of the upper rim. Typically, the limits for the heights apply analogously to electronic components which are arranged in a lower cavity, present in some embodiments, in relation to the edge of the lower rim.

By means of the height limits, the components are received in a protected arrangement and a flat or uniform profile of the receiver is created.

In typical receivers, the coil area or the further layers of the coil area forms a lower rim on an underside of the circuit board, which lower rim on the underside encircles a lower cavity in the inner area.

In some embodiments of receivers, electronic components can be enclosed by the base membrane or by the further layers of the coil area, or the base membrane can be integrated in particular in the layers in the inner area.

The circuit board is typically formed in one piece. In alternative embodiments, at least two circuit boards are provided, where an extra one can be provided for the coil. It is possible to use collapsible, adhesively bonded rigid-flex constructions. In the process of producing the circuit board, this arrangement results in a base membrane in which further layers were built up on the underside. In typical embodiments, only a lower cavity is initially created or no cavity. The upper side of the circuit board is thus easier to populate. In addition to inner area and coil area, the circuit board also has a flexible area. By means of this flexible area, after the electronic components have been fitted it is possible for a further coil area to be folded across the circuit board and adhesively bonded. This embodiment permits a higher inductance of the coil or also a higher current load. Polyimide can be used as material for the flexible area.

Typical receivers comprise a feedback device which works without radio waves and which is designed to generate feedback concerning an operating state of an implant attached to the receiver. The feedback device is typically arranged in the lower cavity or in the upper cavity. It can also typically be enclosed by the base membrane or the coil area or can be integrated in the inner area, in particular in the layers of the base membrane.

A possible operating state can be the functionality of an implant attached to the receiver or a direction of movement of a drive of an implant attached to the receiver.

Typical receivers comprise a switch for changing the operating state of the implant attached to the receiver. Typical switches include: reed contact, photodiode or electromechanical press switch. Typical switches are free of electromagnetic radiation and are thus independent of radio wave transmission, for which the coil can typically be used.

In typical embodiments, the upper cavity or the lower cavity is filled with a resin-catalyst mix. The upper rim or lower rim in the coil area can in this case serve as a mold. Both cavities are typically filled.

Typical receivers are encapsulated with a biocompatible material, for example silicone or epoxy resin. In some embodiments, a glass housing would also be possible, or a ceramic housing in the form that half shells are bonded or welded to each other.

So as not to damage the biocompatible material, the edges of the printed circuit board are provided with a radius in some embodiments of receivers. In this way, sharp edges can be avoided and implantability can be enhanced.

During the building up of the further layers, the inner area of the base membrane is typically covered by a protective sheet on at least one of upper side and underside. Typical protective sheets comprise Teflon, for example, or are made of Teflon. The protective sheet can be arranged in a prepreg cut out in the inner area or in an insulation sheet cut out in the inner area.

The circuit board can be produced using known production methods from printed circuit board technology for producing multilayer circuit boards which permit integration of the coil in the circuit board or also permit a selective generation of height levels.

In typical embodiments, after the circuit board has been finished and, if appropriate, the cavity or cavities have been milled out, a soldering paste is applied in the cavity. This can be done, for example, by jet printing or dispensing.

Typical methods also include populating the inner area on the upper side with electronic components, filling the upper cavity with a resin-catalyst mix, or encapsulating the receiver with a biocompatible material.

Typically, at least 10 layers, typically at least 20 layers or at least 24 layers are provided in the coil area. Typical embodiments comprise at most 100 layers, typically at most 50 layers. Typical coils comprise at least 50 turns, at least 100 turns, or at least 160 turns. The coil typically comprises at most 500 turns or at most 200 turns.

Typical advantages of embodiments are a compact structure with much enhanced functionality or optimized efficiency compared to known receivers of active implants. Typical receivers have a height of less than 5 mm or of less than 4 mm. The step of the upper rim is typically at least 1 mm or at least 2 mm. Typical heights of the lower rim are a maximum of 1 mm or a maximum of 0.5 mm. Typical diameters are at least 15 mm or at least 20 mm or at most 30 mm or at most 50 mm. The thickness of the base membrane is typically at least 5% or at least 7% or at most 20% or at most 15% of the overall height of the receiver.

In typical receiver embodiments, more functions can be integrated. Soldering of the coil can be avoided, for example the risk of polarity reversal can be reduced.

Typical embodiments are more robust, since fewer individual parts are used. Moreover, the coil as an integral module of the circuit board is more protected, and the components inside the cavities are also better protected.

For some embodiments, fewer assembly steps are needed than in known receivers from the prior art, or the assembly can be done more cost-effectively.

BRIEF DESCRIPTION OF THE DRAWINGS

Further advantages and features of preferred embodiments of the invention are explained below with reference to the attached drawings, in which.

DESCRIPTION OF PREFERRED
ILLUSTRATIVE EMBODIMENTS

Typical embodiments are described below with reference to the figures. The invention is not limited to the illustrative embodiments. Instead, the scope of the invention is defined by the claims.

Figure 1:
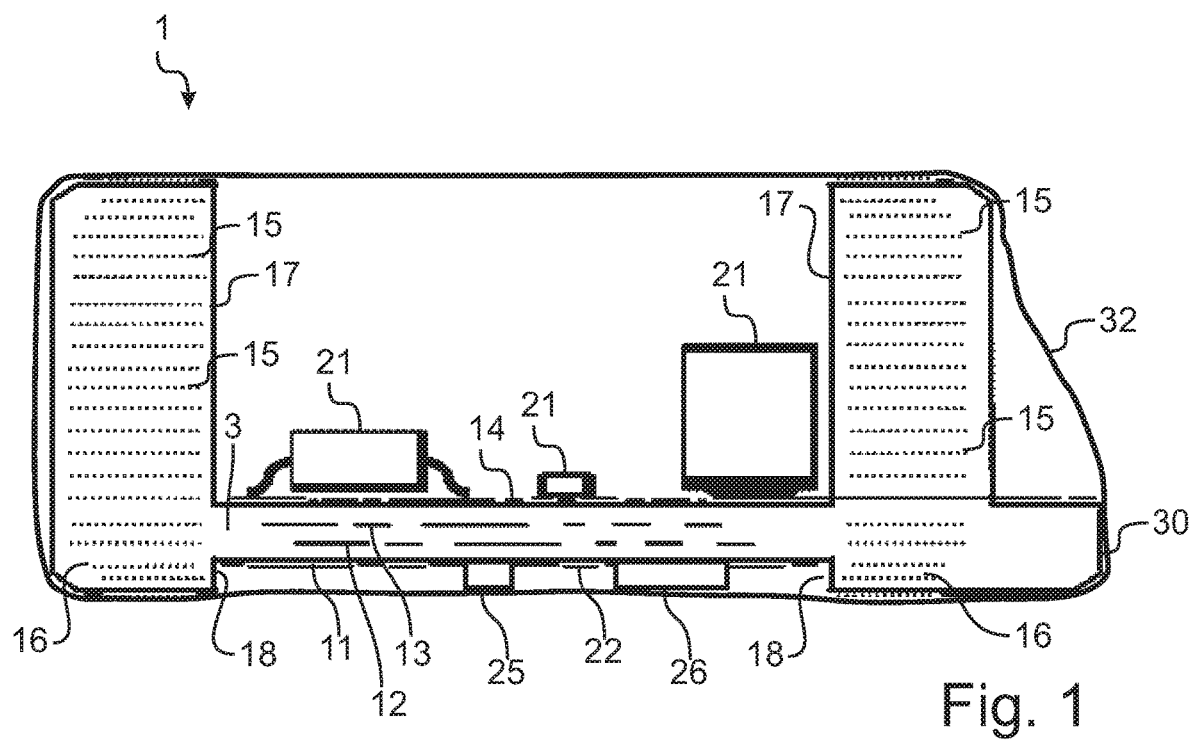
FIG. 1 is a schematic sectional view of an embodiment of the invention.

FIG. 1 shows a receiver 1, which can be part of an implant system that can comprise an electromechanical implant (not shown in the figures) attachable to the receiver 1.

The receiver 1 is implantable and suitable for transmitting energy to the implant. For this purpose, the receiver 1 comprises a coil, which is suitable for transmitting or receiving energy sufficient to power an electromechanical drive of an implant, for example of an intramedullary nail, as is shown in DE 10 2011 053 638 A1 for example, or of a scoliosis treatment unit, as is shown in DE 10 2010 047 738 A1 for example.

The receiver 1 is suitable for transmitting a constant rating of at least 1W to an active or mechatronic implant.

The receiver 1 comprises a multi-layer circuit board, which comprises a base membrane 3 extending horizontally across the entire cross section of the circuit board. The base membrane comprises four layers 11-14, which are designed as electrically conductive, structured copper layers.

In an outer coil area, the circuit board has fifteen upper further layers 15 forming an upper rim 17, and three lower further layers 16 forming a lower rim 18. For the sake of clarity, not all of the further layers are provided with reference signs.

The rims 17 and 18 each extend circumferentially around an inner area in which only the four layers 11-14 of the base membrane are present.

Prepregs are arranged as insulation sheets between all of the layers 11-16, wherein the outermost layers 11 and 14 in the inner area lie exposed such that, on an upper side of the base membrane (layer 14) and on an underside of the base membrane (layer 11), it is possible to arrange electronic components, which are shown by way of example on the upper side by reference signs 21, or contacts 22.

In the coil area, the layers 11-16, i.e. the layers 11-14 of the base membrane and the upper and lower further layers 15 and 16, form coil turns of the coil. Seven turns (shown only schematically in FIG. 1) are arranged on each layer 11-16. In this way, the coil is incorporated integrally in the layers of the circuit board in the coil area.

In some embodiments, embedded parts can be integrated in the base membrane in the inner area. Moreover, packaged or unpackaged components, ICs, transistors or resistors can be arranged there. In particular, test points can be provided on the underside or on the upper side in order to make it easier to test the receiver before it is encapsulated with silicone. Furthermore, receivers in some embodiments can be provided with a ferrite sleeve around the coil area or a paste in order to improve the efficiency of the coil.

In typical embodiments, the circuit board comprises printed circuit board materials known from the prior art, for example FR4 or polyimide.

An upper cavity is formed in the inside of the upper rim 17. A lower cavity is formed in the inside of the lower rim 18. The electronic components 21 of the embodiment shown do not protrude above the upper rim 17. This means that the electronic components 21 have an overall height lower than the height of the top of the rim 17 above the surface of the upper side of the base membrane.

In some embodiments, the height of the rim can be defined as the height between the exposed layer, or uppermost/lowermost layer, of the inner area and the top of the rim.

A piezo buzzer 26 arranged in the lower cavity protrudes past the lower rim 18 only by 10% of the height of the lower rim beyond the exposed layer 11 of the underside of the base membrane. A compact structure is obtained in this way.

A lug 30, formed from the layers 11-14 of the base membrane and from the lower additional 16, is provided on one side. The lug 30 can be used with the exposed layer 14 for contacts, for example for attachment of the implant.

The cavities formed by the rims 17 and 18 are filled with a resin-catalyst mix. The entire receiver 1 is encapsulated with silicone 32, such that it is biocompatible.

Figure 2:
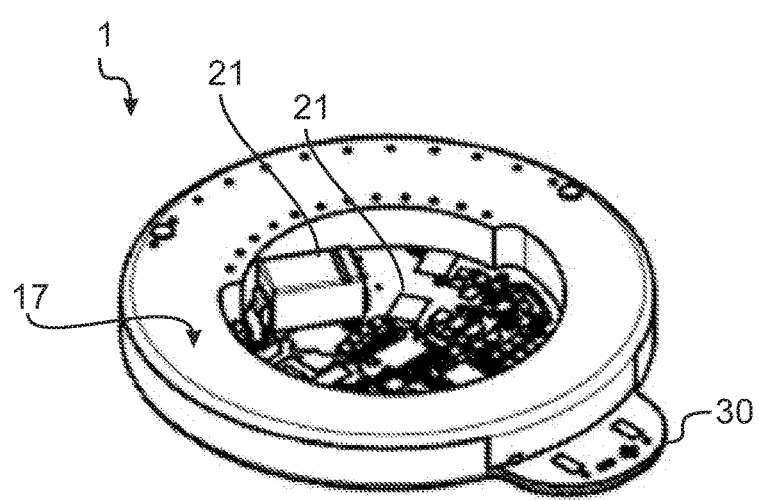
FIG. 2 shows a further embodiment in a perspective schematic view.

FIG. 2 shows a further embodiment of a receiver 1 for a mechatronic implant. The cavities of the receiver 1 in FIG. 2 are not yet filled with resin-catalyst mix, and the silicone layer is also missing.

The perspective view in FIG. 2 shows clearly how the upper rim 17 encircles an inner area in which electronic components 21 can be arranged and protected.

In typical embodiments, electronic components are arranged in the inner area on the upper side or underside, or both, of the base membrane. The arrangement offers good protection against mechanical influences.

Figure 3:
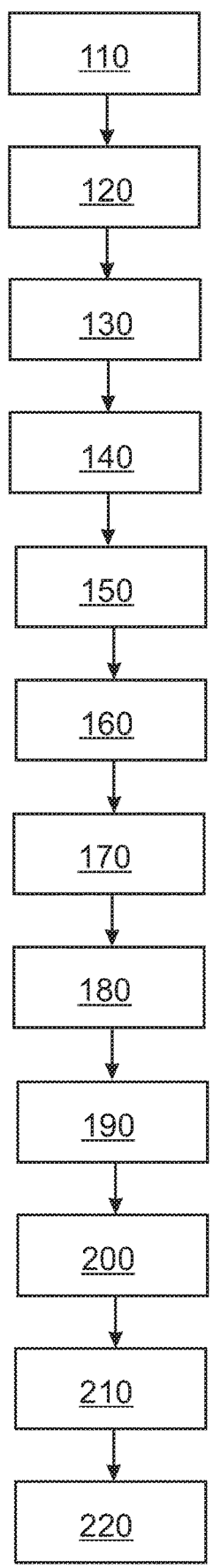
FIG. 3 shows the sequence of a method according to the invention.

FIG. 3 shows a typical method for producing a receiver. The method starts in block 110, where a four-layer base membrane is produced. Structured layers of copper (cores) and insulation sheets (prepregs) are then alternately applied and press-molded.

The base membrane is composed of four copper sheets (the layers) and three insulation sheets, which are structured, bored and electroplated. In the finished receiver, the upper copper sheet forms the layer on the upper side of the base membrane in the upper cavity, on which layer the components are fitted. In the finished product, the test points are located on the lowermost layer of the base membrane.

In a block 120, a prepreg milled out in the inner area, i.e. in the area of the cavities, is placed on the upper side and the underside of the base membrane.

In a block 130, Teflon disks are inserted into these milled-out areas. In contrast to the insulating material, these disks do not connect to the copper sheet of the outermost layers of the base membrane.

In a block 140, further layers and prepregs are applied as insulating material to the upper side and to the underside of the base membrane. The respectively outermost sheet is insulating material.

In a block 150, a contour is milled in the resulting unpopulated circuit board, the milling being carried out to the depth of the Teflon disk. This results in a cavity on the upper side and a cavity on the underside of the unpopulated circuit board.

In a block 160, the Teflon disks are removed from the unpopulated circuit board.

In a block 170, the surfaces of the cavities are finished with a thin sheet of nickel (e.g. 3-10 nm) and a thinner sheet of gold (ca. 0.5-3 nm).

In a block 180, a soldering paste is applied to the finished surfaces of the cavities, e.g. by jet printing or dispensing.

In a block 190, the footprints, i.e. landing areas provided for components, in the cavities are populated with electronic components.

In a block 200, the soldering tin under the feet of the electronic components melts in the soldering furnace, typically with a vapor phase, in order to obtain uniform heat distribution, and the structural parts connect to the circuit board.

In a block 210, the cavities are filled with a resin-catalyst mix until the cavities are at least substantially full to the top. Typically, no potting mold is used for this purpose. The potting is typically carried out without a potting mold.

In a block 220, the circuit board thus obtained is encapsulated with silicone in order to make the receiver with the circuit board biocompatible. With that, the method shown in FIG. 3 is completed.

The invention claimed is:

1. An implantable receiver for transmitting energy to an implant, with
   a multi-layer circuit board comprising a plurality of electrically conductive layers, wherein the circuit board comprises an outer coil area and a multi-layer inner area enclosed by the coil area, wherein the plurality of electrically conductive layers in the multi-layer inner area define the multi-layer circuit board in the inner area, a coil which is integrally incorporated at least partially in the layers of the circuit board in the coil area, wherein the number of the layers of the circuit board is smaller within this inner area than in the coil area, wherein the coil area, on an upper side of the circuit board, forms an upper rim around the inner area, and wherein electronic components are arranged on the upper side of the circuit board in the inner area, and wherein the coil area forms a lower rim on an underside of the circuit board, which lower rim on the underside encircles a lower cavity in the inner area.

2. The receiver according to claim 1, wherein the inner area comprises at most half as many layers as the coil area.

3. The receiver according to claim 1, wherein the circuit board is formed in one piece.

4. The receiver according to claim 1, with a feedback device which works without radio waves and which is designed to generate feedback concerning an operating state of an implant attached to the receiver.

5. The receiver according to claim 1, wherein the cavity or the cavities are filled and/or the receiver is encapsulated with a biocompatible material.

6. The receiver according to claim 1, wherein the circuit board comprises a multi-layer base membrane which extends across both the inner area and the coil area, wherein layers of the base membrane define the plurality of electrically conductive layers in the inner area and a portion of the plurality of electrically conductive layers in the coil area.

7. An implantable system with an electromechanical implant and an implantable receiver for transmitting energy to the implant, with a multi-layer circuit board comprising a plurality of electrically conductive layers, wherein the circuit board comprises an outer coil area and a multi-layer inner area enclosed by the coil area, wherein the plurality of electrically conductive layers in the multi-layer inner area define the multi-layer circuit board in the inner area, a coil which is integrally integrated at least partially in the layers of the circuit board in the coil area, wherein the number of the layers of the circuit board is smaller within this inner area than in the coil area, wherein the coil area, on an upper side of the circuit board, forms an upper rim around the inner area, and wherein electronic components are arranged on the upper side of the circuit board in the inner area, and wherein the coil area forms a lower rim on an underside of the circuit board, which lower rim on the underside encircles a lower cavity in the inner area.

8. A method for producing an implantable receiver for transmitting energy to an implant and comprising a circuit board, by:

producing a multi-layer base membrane of the circuit board with a plurality of layers;

building up further layers on an upper side and an underside of the base membrane;

wherein turns of a coil are integrated at least in some of the further layers in a coil area;

creating an upper cavity and a lower cavity in the inner area to the inside of the coil area, by removing the further layers in the inner area; and populating the inner area with electronic components.

9. The method according to claim 8, wherein the inner area of the base membrane is covered, on at least one of upper side and underside, by a protective layer during the building up of the further layers.

10. The method according to claim 8, further comprising:

the populating step comprises populating the inner area with electronic components on the upper side, and filling the upper cavity with a resin-catalyst mix.

11. The method according to claim 8, further comprising: encapsulating the receiver with a biocompatible material.

\* \* \* \* \*